United States Patent
Mayer et al.

(10) Patent No.: US 9,683,918 B2
(45) Date of Patent: Jun. 20, 2017

(54) WEAR DETECTION SYSTEMS FOR OVERHEAD CONVEYOR SYSTEMS

(71) Applicant: Toyota Motor Engineering & Manufacturing North America, Inc., Erlanger, KY (US)

(72) Inventors: Dennis L. Mayer, Evansville, IN (US); Matthew R. Allen, Vincennes, IN (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 355 days.

(21) Appl. No.: 14/154,849

(22) Filed: Jan. 14, 2014

(65) Prior Publication Data

US 2015/0197399 A1    Jul. 16, 2015

(51) Int. Cl.
  *B65G 43/02*   (2006.01)
  *G01N 3/56*    (2006.01)
  *B61B 3/00*    (2006.01)
  *G01M 5/00*    (2006.01)
  *G01B 11/06*   (2006.01)

(52) U.S. Cl.
  CPC ............. *G01N 3/56* (2013.01); *B61B 3/00* (2013.01); *G01B 11/06* (2013.01); *G01M 5/0025* (2013.01); *G01M 5/0033* (2013.01)

(58) Field of Classification Search
  CPC ........ G01B 7/14; G01M 5/033; B61L 23/045; B61L 23/047
  USPC .............................................................. 73/7
  See application file for complete search history.

(56) References Cited

U.S. PATENT DOCUMENTS

| | | | | |
|---|---|---|---|---|
| 3,811,556 A | * | 5/1974 | Kaiser .................... | B65G 21/22 193/38 |
| 3,861,315 A | * | 1/1975 | Rypinski ................. | B61D 3/20 104/125 |
| 3,997,639 A | * | 12/1976 | Rochelle ............ | B28B 19/0038 264/135 |
| 4,625,412 A | * | 12/1986 | Bradshaw ............... | B61K 9/08 33/1 Q |
| 4,791,871 A | * | 12/1988 | Mowll ..................... | B60L 5/40 104/88.02 |

(Continued)

FOREIGN PATENT DOCUMENTS

EP    2487124    8/2012
JP    6-209187   7/1994

(Continued)

OTHER PUBLICATIONS

Geismar, Measure Measurement, Societe Des Anciens Establissements. Jan. 2010.*

*Primary Examiner* — Natalie Huls
*Assistant Examiner* — Monica S Young
(74) *Attorney, Agent, or Firm* — Dinsmore & Shohl LLP (57) ABSTRACT

A wear detection system for detecting beam wear along a support flange of a beam includes a rail riding portion configured to travel along the support flange and a processor portion connected to the rail riding portion. The rail riding portion includes a wear measurement system comprising one or more measuring sensors configured to provide an output indicative of thickness of the support flange. The processor portion includes an integrated processing system that receives the output of the one or more measuring sensors and generates measurement information based on the output.

19 Claims, 10 Drawing Sheets

(56) References Cited

U.S. PATENT DOCUMENTS

| | | | | |
|---|---|---|---|---|
| 5,009,014 | A * | 4/1991 | Leach | B61K 9/08 33/1 Q |
| 5,199,176 | A * | 4/1993 | Theurer | B61K 9/08 33/1 Q |
| 5,465,668 | A * | 11/1995 | Tarassoff | B61B 7/02 104/112 |
| 5,563,392 | A * | 10/1996 | Brown | B65G 43/02 235/91 R |
| 6,170,401 | B1 * | 1/2001 | Miller | E01B 29/09 104/12 |
| 6,192,736 | B1 * | 2/2001 | Clem | B61K 9/08 73/10 |
| 6,672,223 | B1 * | 1/2004 | Date | B61B 13/04 104/106 |
| 6,983,834 | B1 * | 1/2006 | Kraudy | B60M 1/302 191/22 DM |
| 7,036,232 | B2 * | 5/2006 | Casagrande | B61K 9/08 15/250.001 |
| 7,111,722 | B2 | 9/2006 | Burch | |
| 7,475,770 | B1 | 1/2009 | Strange et al. | |
| 7,659,972 | B2 * | 2/2010 | Magnus | B61K 9/08 356/237.1 |
| 8,260,574 | B1 | 9/2012 | Schuitema | B65G 43/02 198/571 |
| 2002/0073876 | A1 * | 6/2002 | Einar | B61B 13/04 104/125 |
| 2004/0081540 | A1 * | 4/2004 | Uebach | B65G 63/025 414/395 |
| 2004/0122569 | A1 * | 6/2004 | Bidaud | B61K 9/08 701/19 |
| 2004/0149158 | A1 * | 8/2004 | Keller | B61B 3/02 104/89 |
| 2005/0238467 | A1 * | 10/2005 | Minges | B65G 1/0492 414/462 |
| 2007/0064244 | A1 * | 3/2007 | Mian | G01B 11/25 356/601 |
| 2007/0124035 | A1 * | 5/2007 | Hasenfuss | B61B 5/02 701/19 |
| 2007/0131133 | A1 * | 6/2007 | Andreasen | B61K 1/00 104/89 |
| 2007/0163352 | A1 * | 7/2007 | Nielsen | B61K 9/10 73/668 |
| 2009/0132179 | A1 * | 5/2009 | Fu | G01M 99/007 702/34 |
| 2009/0188406 | A1 * | 7/2009 | Sperling | E01B 29/26 104/307 |
| 2009/0319197 | A1 * | 12/2009 | Villar | B61K 9/08 702/34 |
| 2012/0218868 | A1 * | 8/2012 | Kahn | G01N 29/265 367/99 |
| 2012/0257195 | A1 * | 10/2012 | Scherf | B61K 9/08 356/237.1 |
| 2013/0047729 | A1 * | 2/2013 | Wigh | G01N 29/043 73/636 |
| 2013/0160309 | A1 * | 6/2013 | Logan | G01B 11/00 33/228 |
| 2014/0123871 | A1 * | 5/2014 | Dehmel | B61D 3/18 105/329.1 |
| 2014/0142868 | A1 * | 5/2014 | Bidaud | G01N 21/8803 702/40 |
| 2015/0298578 | A1 * | 10/2015 | Parsons | B60M 1/307 191/44.1 |
| 2016/0075533 | A1 * | 3/2016 | Scomparin | B66B 9/003 187/240 |

FOREIGN PATENT DOCUMENTS

| | | |
|---|---|---|
| JP | 2004012174 A | 1/2004 |
| JP | 2004279076 A * | 10/2004 |
| JP | 2008249508 A * | 10/2008 |

* cited by examiner

| SECTION 18 ||||
|---|---|---|---|
| FLANGE 156 || FLANGE 158 ||
| LOCATION (mm) | VALUE (mm) | LOCATION (mm) | VALUE (mm) |
| 50 | 6.28 | 50 | 5.07 |
| 100 | 6.43 | 100 | 4.33 |
| 150 | 6.07 | 150 | 2.28 |

| 1000 | 5.98 | 1000 | 3.90 |
|---|---|---|---|
| 1050 | 6.01 | 1050 | 3.01 |
| 1100 | 6.12 | 1051 | 1.95 |
| 1150 | 5.94 | 1100 | 2.79 |

WEAR DETECTION SYSTEMS FOR OVERHEAD CONVEYOR SYSTEMS

TECHNICAL FIELD

The present specification generally relates to wear detection systems and, more particularly, to wear detection systems that assess wear on overhead conveyor systems.

BACKGROUND

While there are a variety of overhead rail systems, some overhead rail systems are of a free rail type including a load track portion and a power track portion. The load track portion may include free rail members oriented face-to-face that provide a track for a load carrying trolley. The power track portion may include a propelling chain and pushers for a power line that is used to move the load carrying trolleys along the track.

The free rail members typically include opposing support flanges. The load carrying trolleys may have wheels that ride along the opposing support flanges of the free rail members. Due to continued use under loaded conditions, the wheels of the load carrying trolleys can wear the support flanges of the free rail members such that the support flanges become thin and eventually lose their structural support in certain areas.

Currently, inspection may be accomplished by manually measuring the support flanges of the free rail members at different locations along the length of the track. This might require an inspector to climb a ladder and measure the thickness of the support flanges, for example, using a handheld thickness gauge. Such reading can be subject to variance due to each individual's technique and precise location of the thickness gauge. Other wear detection systems and methods are desired.

SUMMARY

In one embodiment, a wear detection system for detecting beam wear along a support flange of a beam includes a rail riding portion configured to travel along the support flange and a processor portion connected to the rail riding portion. The rail riding portion includes a wear measurement system comprising one or more measuring sensors configured to provide an output indicative of thickness of the support flange. The processor portion includes an integrated processing system that receives the output of the one or more measuring sensors and generates measurement information based on the output.

In another embodiment, a method for detecting beam wear along a support flange of a beam using a wear detection system is provided. The method includes moving a rail riding portion of the wear detection system along the support flange. The wear detection system includes a processor portion connected to the rail riding portion. An output is generated indicative of thickness of the support flange using one or more measuring sensors of a wear measurement system carried by the rail riding portion. Measurement information is generated using an integrated processing system of the processor portion using the output of the one or more measuring sensors.

In another embodiment, a wear analysis system for detecting beam wear along a support flange of a beam includes a wear detection system. The wear detection system includes a rail riding portion configured to travel along the support flange and a processor portion connected to the rail riding portion. The rail riding portion includes a wear measurement system comprising one or more measuring sensors configured to provide an output indicative of thickness of the support flange. The processor portion includes an integrated processing system that receives the output of the one or more measuring sensors and generates measurement information based on the output. A computer external to the wear detection system receives the measurement information and reports the measurement information to a user.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Embodiments described herein generally relate to wear detection systems that assess wear on overhead conveyor systems. The wear detection systems may be used to detect rail wear in overhead rail systems including free rail members oriented face-to-face that provide a track for a load carrying trolley. The wear detection systems may generally include a rail riding portion and a portable processor portion that is carried by and suspended from the rail riding portion.

The rail riding portion is not only configured to ride along the overhead rail system, but can also support sensors and other devices that provide information to a processor of the portable processor portion for processing and analysis to detect amount of wear and location in the overhead conveyor system of the wear.

Figure 1:
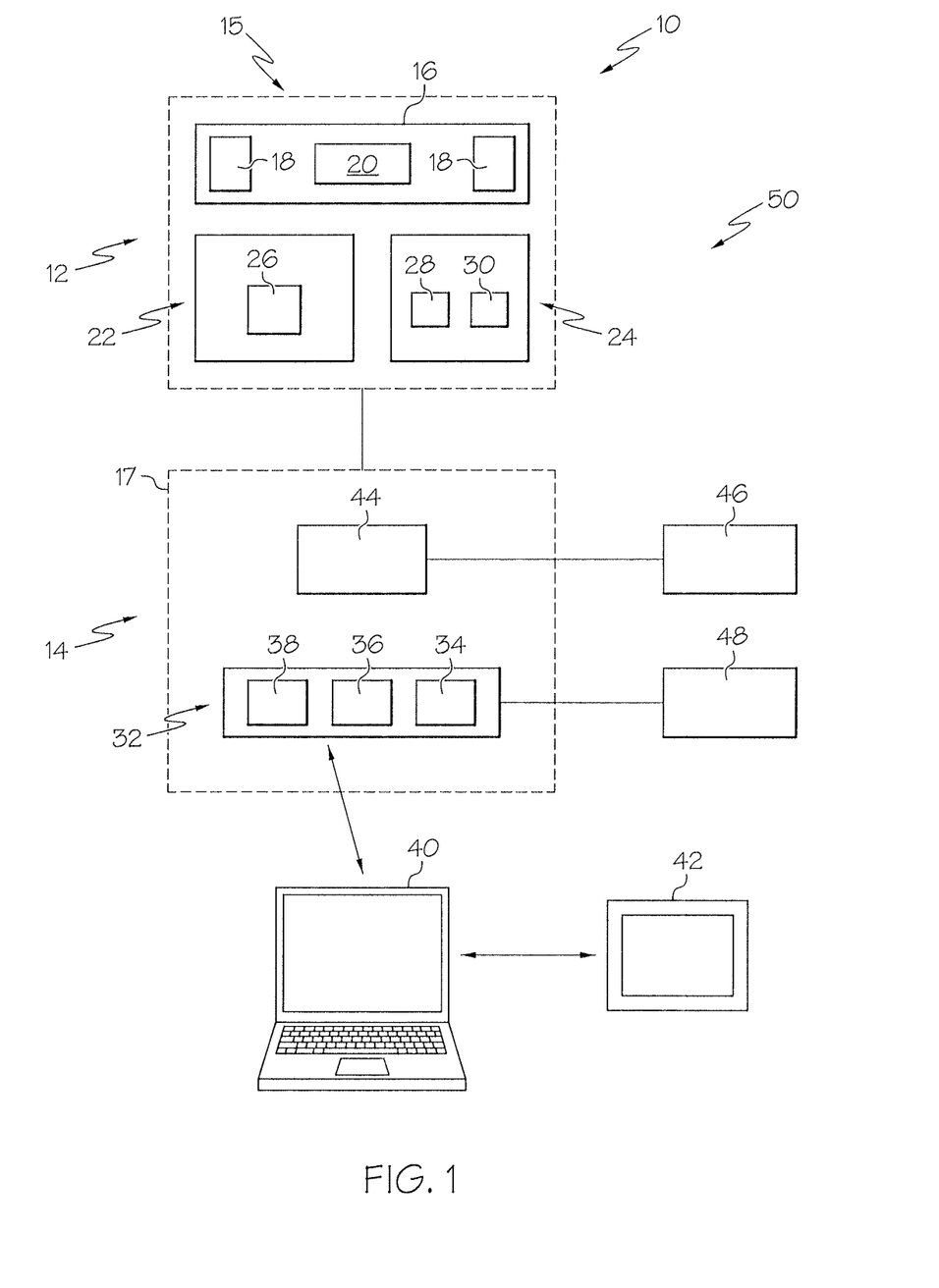
FIG. 1 is a diagrammatic illustration of a wear analysis system including a wear detection system and an external computer according to one or more embodiments described herein.

Referring to FIG. 1, a wear detection system 10 is illustrated diagrammatically and includes a rail riding portion 12 and a processor portion 14 connected to the rail riding portion 12. The rail riding portion 12 includes a drive system 15, which, as will be described in greater detail below, may include a frame 16, wheels 18 and a motor 20 that is used to drive the wheels 18 to allow the wear detection system 10 to travel along the rail members. In some embodiments, the drive system 15 may utilize a power rail of the overhead conveyor system to drive the wheels 18 to allow the wear detection system 10 to travel along the rail members. In these embodiments, a separate motor may or may not be used and a connector assembly, also represented by element 20, may be provided for connecting to a power line supported by the power rail.

The wear detection system 10 further includes a wear measurement system 22 and a location detection system 24. The wear measurement system 22 includes one or more measuring sensors 26, such as two pairs of synchronized measuring sensors that are used in detecting wear along the rail members. In some embodiments, as an example, the measuring sensors 26 may include opposing photoelectric sensors, such as laser displacement sensors; however, other sensor types may be used. The location detection system 24 includes one or more detecting sensors 28, such as one sensor that is used in detecting location of the wear detection system 10 within the overhead conveyor system. In an embodiment, as an example, the detecting sensor 28 may include a line-type sensor that can be used to measure width of an object. An encoder 30 (e.g., a rotary encoder) may be provided that is also used in providing location information for the wear detection system 10. While the drive system 15, wear measurement system 22 and location detection system 24 are illustrated at the rail riding portion 12 for illustrative purposes, they or components thereof may be located at the processor portion 14. As will be described in greater detail below, the location detection system 24 may utilize the detecting sensor 28 for identifying what section or region the wear detection system 10 is moving into and the encoder 30 may be used to more finely locate the wear detection system 10 within a particular section of the overhead conveyor system.

The processor portion 14 generally houses processing components of the wear detection system 10. The processor portion 14 includes a housing 17, which may be a fully or partially enclosed housing with one or more access doors or panels. In some embodiments, the panels may be formed of a lightweight material, such as aluminum and/or plastic. In some embodiments, one or more of the panels may be transparent or translucent to facilitate viewing of contents within the housing 17. An integrated processing system 32 may be provided within the housing 17 for receiving and processing information from the various components of the wear measurement system 22 and location detection system 24. For example, the integrated processing system 32 (e.g., commercially available from Rockwell Automation, Inc.) may include a programmable logic controller (PLC) module 34 for data monitoring and recording in memory. The PLC module 34 may use both discrete and analog input modules for data and control functions as well as a high speed counter module 36 for tracking encoder data. The integrated processing system 32 may further include a communications module 38 that allows for wired or wireless communication with an external computer 40 or other device, such as a mobile computing device 42 (e.g., smart phone, tablet, etc.). As such, the wear detection system 10 may be part of a wear analysis system 50 that includes the wear detection system 10 and one or more computing devices 40 and 42 capable of communicating and receiving wear information from the wear detection system 10. A power supply 44 (e.g., NiCad batteries or other battery types) may be used to power the integrated processing system 32 and any other electronics of the wear detection system 10. In some embodiments, an external charger 46 is provided for recharging the power supply 44. An external power supply 48 may be provided to maintain power to the integrated processing system 32 when the wear detection system 10 is not in use. Such an arrangement can allow user access to data processed or otherwise saved in memory of the integrated processing system 32, even when the wear detection system 10 is not carrying out a wear detection operation.

Figure 2:
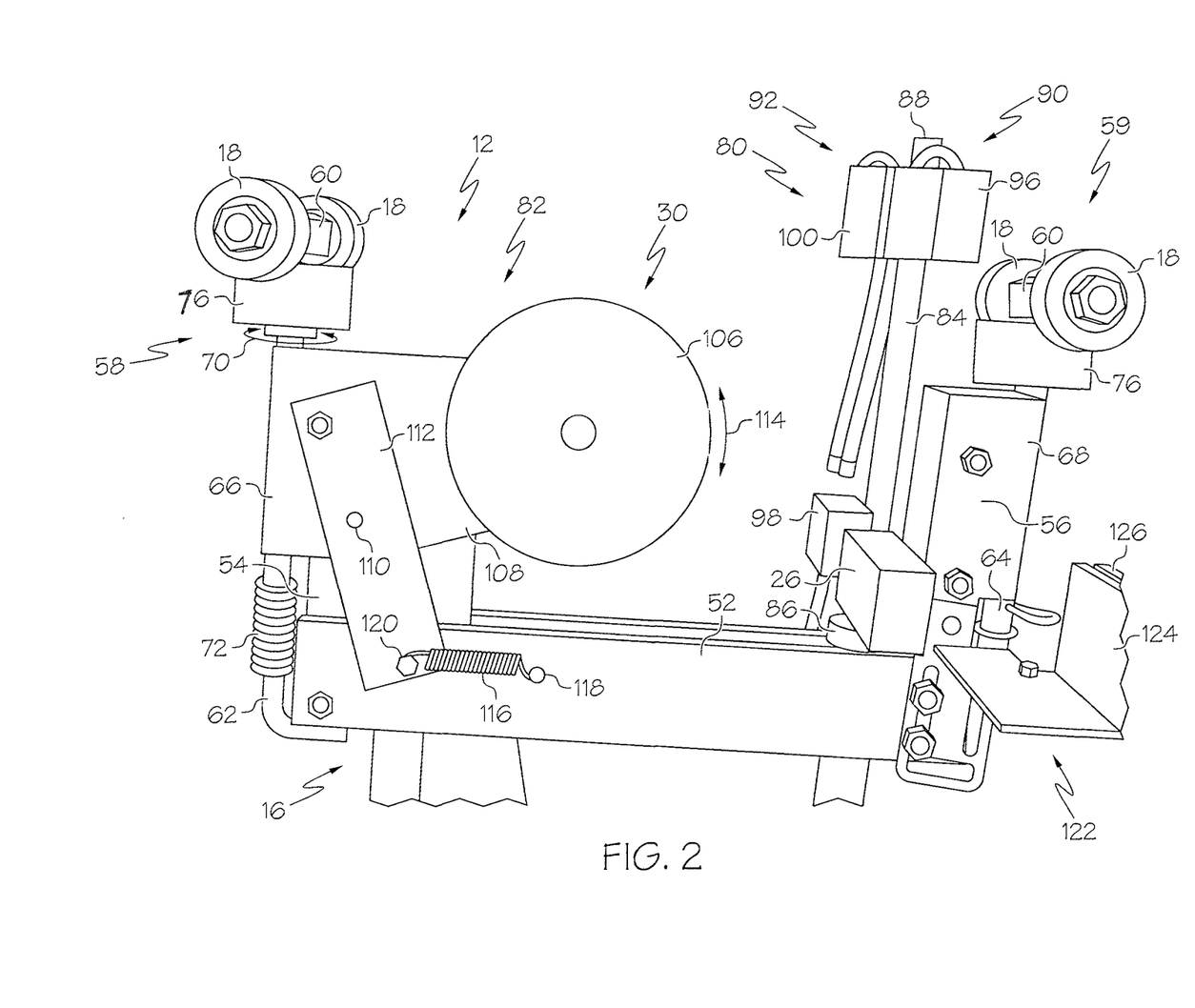
FIG. 2 is a side view of a rail riding portion of the wear detection system of FIG. 1 according to one or more embodiments described herein.

Referring to FIG. 2, the rail riding portion 12 is illustrated in isolation and includes the frame 16 that supports various components of the rail riding portion 12 thereon. The frame 16 includes a base support member 52 that extends between upright support members 54 and 56. The base support member 52 supports the processor portion 14 (FIG. 1) in a hanging fashion when connected thereto. The wheels 18 are rotatably supported by axles 60 mounted to the upright support members 54 and 56 as wheel mount assemblies 58 and 59. The axles 60 may be mounted to mounting rods 62 and 64 that are, in turn, mounted to the upright support members 54 and 56 using U-shaped brackets 66 and 68. The brackets 66 and 68 may allow pivoting of the axles 60 (e.g., in the direction of arrow 70) to facilitate insertion and removal of the wear detection system 10 from the overhead rail system. One or both of the axles 60 may be spring biased (e.g., by spring 72) so that the axles 60 return and be biased from an insertion position (e.g., rotated about 90 degrees) toward a rail riding position as shown by FIG. 2. Provided on the mounting rods 62 and 64 are positioning structures, such as wheels 76. The positioning wheels 76 may be rotatably mounted to the mounting rods 62 and 64 and are horizontally oriented (as opposed to the vertically oriented wheels 18) to provide horizontal location of the rail riding portion 12 as will be described below.

The frame 16 further supports a sensor mount assembly 80 and an encoder mount assembly 82. The sensor mount assembly 80 includes an upright support member, such as a support bar or rod 84 that is connected at one end 86 to the base support member 52 and extends to a free end 88. Laser displacement sensor pairs 90 and 92 (e.g., commercially available from Keyence Corporation) are mounted to the support rod 94. Laser displacement sensor pair 90 includes the measuring sensor 26 and measuring sensor 96 in a face-to-face relationship and laser displacement pair includes measuring sensor 98 and measuring sensor 100, similarly in a face-to-face relationship, but spaced apart horizontally, such that each laser displacement sensor pair 90 and 92 can be used to measure thickness of adjacent support flanges and provide an output indicative of thickness of each support flange.

The encoder mount assembly 82 includes the encoder 30 with rotary wheel 106 that is rotatably mounted to a pivot arm 108. The pivot arm 108 is, in turn, rotatably mounted to the upright support member 54 at a pivot location 110. A biasing arm 112 is mounted to the pivot arm 108 such that movement of the biasing arm 112 also moves the pivot arm in an up and down, arcuate manner as illustrated by arrow 114. A spring 116 may be provided to bias the rotary wheel 106 in the illustrated extended position. The spring 116 may be attached to the base support member 52 at one end 118 and to the biasing arm 112 at an opposite end 120. Such a biased arrangement for the encoder 30 can maintain contact between the rotary wheel 106 and underside of the rail member.

An object detector mount assembly 122 may also be provided. The object detector mount assembly 122 may include a sensor mount 124 that is connected to the upright support member 56. The detecting sensor 28, such as a photoelectric sensor (e.g., commercially available from Balluff Inc.) may be mounted to the sensor mount 124 at a location adjacent to the base support member 52. As will be described in greater detail below, the detecting sensor 28 is used to detect a yoke of the overhead conveyor system in order to provide location information associated with the measurement information.

Figure 3:
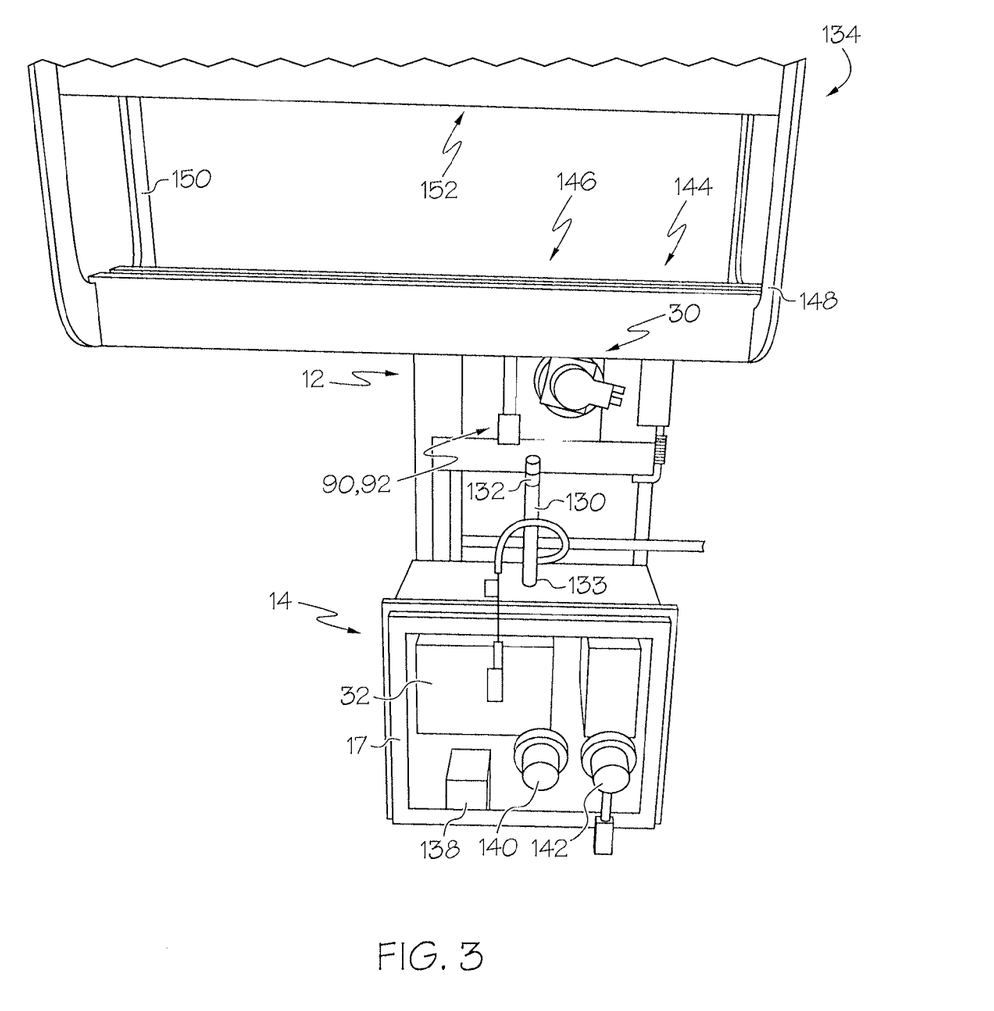
FIG. 3 is a side view of a processor portion of the wear detection system of FIG. 1 according to one or more embodiments described herein.
Figure 4:
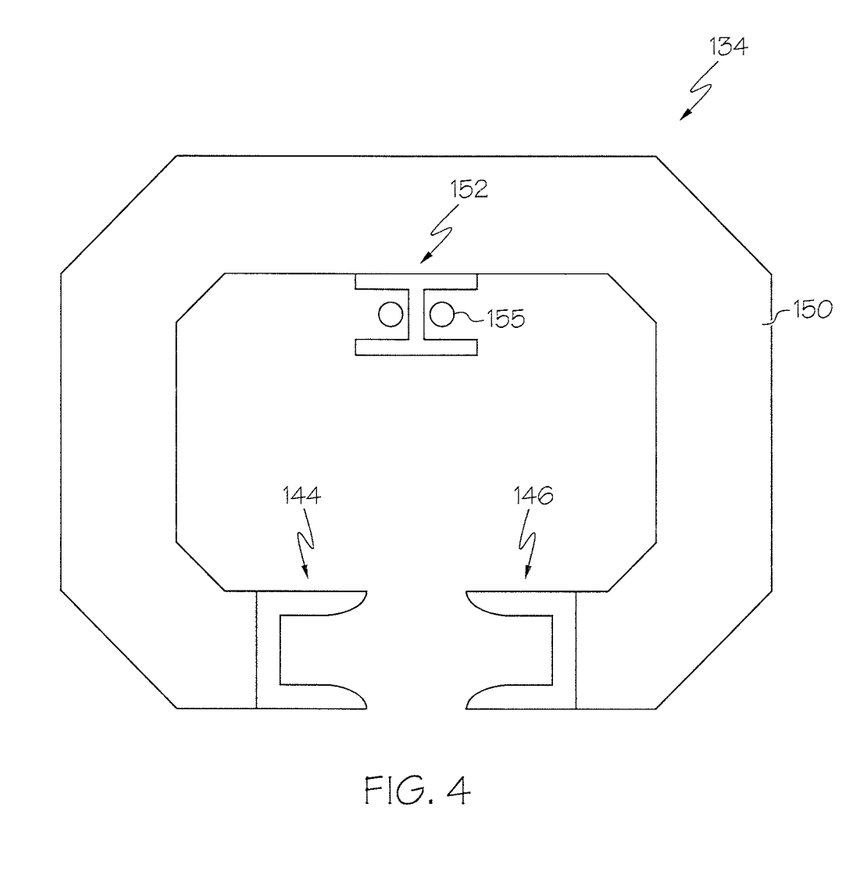
FIG. 4 illustrates diagrammatically an overhead conveyor system according to one or more embodiments described herein.

Referring to FIG. 3, the processor portion 14 is shown connected to the rail riding portion 12 using a rod 130 that is connected at one end 132 to the base support member 52 in a hanging fashion, when the rail riding portion 12 is positioned on an overhead conveyor system 134. Referring also to FIG. 4, the overhead conveyor system 134 includes free rail members 144 and 146 that are held in position by multiple yokes 148 and 150. A power rail 152 in the form of an I-beam is held above the free rail members 144 and 146 to support a propelling chain and pushers for a power line 155 that can be used to move the wear detection system 10 along the free rail members. Referring again to FIG. 3, the other end 133 of the rod 130 is connected to the housing 17, which rides below or underneath the free rail members 144 and 146, providing a rigid connection therebetween that can inhibit any swinging motion of the processor portion 14 relative to the rail riding portion 12 during use. In the illustrated embodiment, the housing 17 includes a transparent panel 138 with the housing 17 being fully enclosed. In some embodiments, the housing 17 may be sealed to inhibit contaminates such as dust or moisture from entering the housing 17.

The integrated processing system 32 is located in the housing 17. The integrated processing system 32 receives measurement output indicative of flange thickness from the laser displacement sensor pairs 90 and 92 and location output from the encoder 30 and the detecting sensor 28 indicative of location along the overhead conveyor system 134. The integrated processing system 32 may be connected to the laser displacement sensor pairs 90 and 92, encoder 30 and detecting sensor 28 using any suitable connection such as wired and/or wireless connections. Batteries 140 and 142 may also be located in the housing to supply power to the sensor pairs 90 and 92, encoder 30, detecting sensor 28 and integrated processing system 32. The batteries 140 and 142 may be, for example NiCad battery packs or any other suitable battery type. The batteries 140 and 142 may be charged using an external charger.

Figure 5:
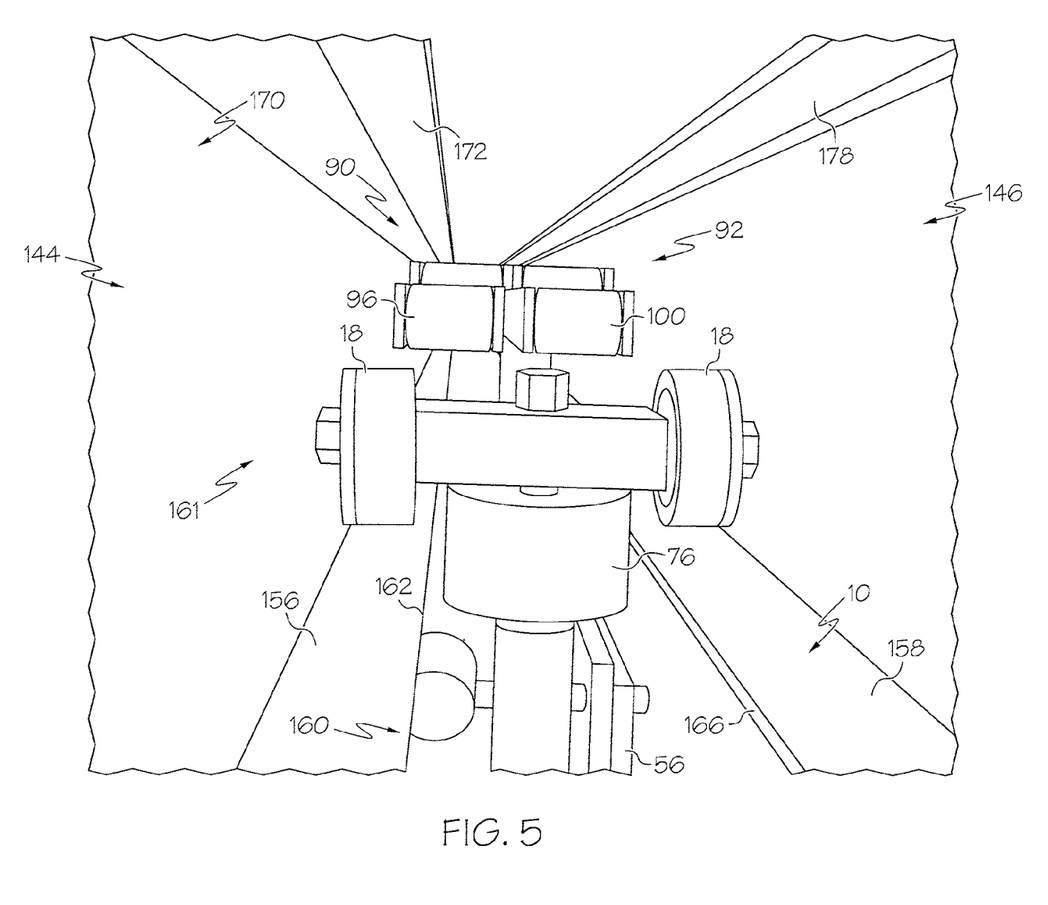
FIG. 5 illustrates operation of the wear detection system of FIG. 1 with the overhead conveyor system of FIG. 4 according to one or more embodiments described herein.
Figure 6:
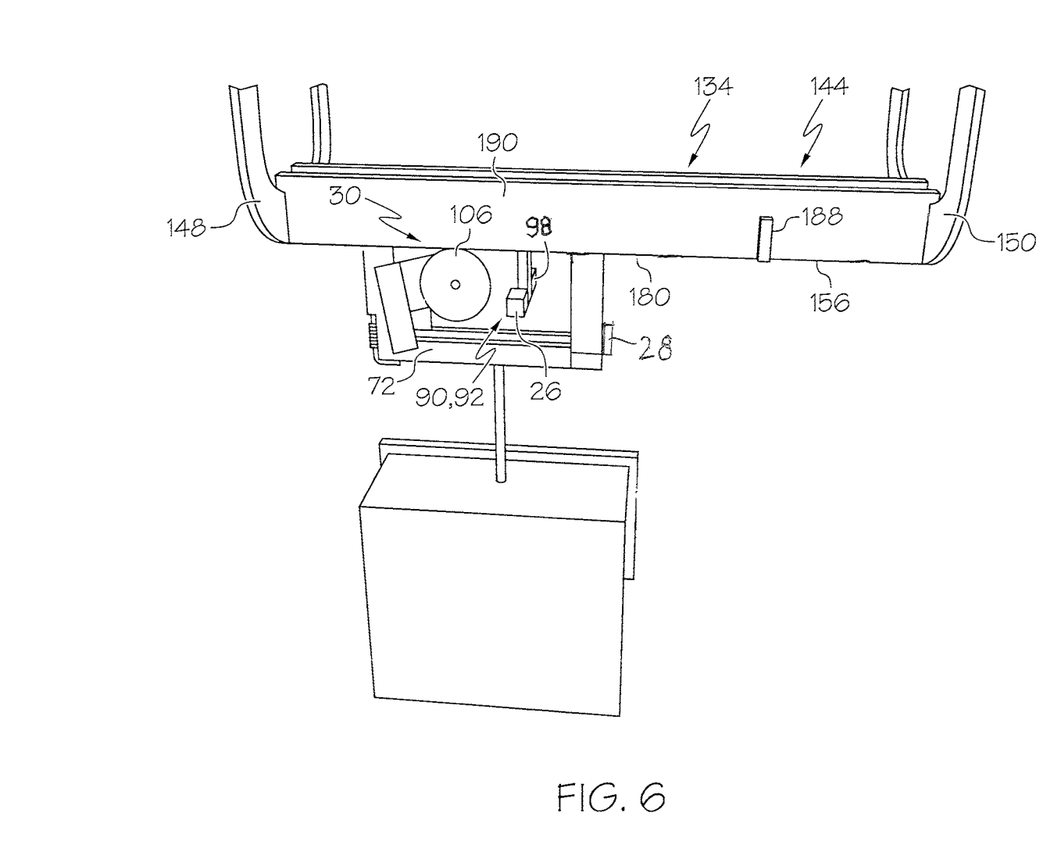
FIG. 6 illustrates operation of the wear detection system of FIG. 1 with the overhead conveyor system of FIG. 4 according to one or more embodiments described herein.

FIGS. 5 and 6 illustrate operation of the wear detection system 10. Referring to FIG. 5, the wheels 18 ride along lower rails or support flanges 156 and 158 of the free rail members 144 and 146. As can be seen, the positioning wheels 76 are located in a gap 160 provided between the support flanges 156 and 158 through which the upright support members 54 and 56 extend. The positioning wheels 76 can aid in alignment of the sensor pairs 90 and 92 for measuring thickness of each support flange 156 and 158 by engaging one or both edges 162 and 166 of the support flanges 156 and 158 and maintaining a substantially constant widthwise position as the wear detection system travels along the support flanges 156 and 158. The measuring sensors 96 and 100 can be seen in FIG. 5 and are illustrated above the support flanges 156 and 158. Measuring sensor 96 is at least partially located within a C-shaped channel 170 and between the support flange 156 and flange 172 and measuring sensor 100 is at least partially located within a C-shaped channel 176 and between support flange 158 and flange 178. The spaced formed by the C-shaped channels 170 and 176 may be referred herein as a conveyor support volume 161. Referring to FIG. 6, measuring sensor 26 is located underneath the support flange 156 and measuring sensor 98 is located underneath the support flange 172. Synchronous sampling of the sensor pairs 90 and 92 can occur within 0.00001 s for determining thickness of their respective support flanges 156 and 158 at a particular location along the length of the overhead conveyor system 134.

As can be seen by FIG. 6, the rotary wheel 106 of the encoder 30 is in contact with an underside 180 of the support flange 156. The bias provided by the spring 72 facilitates constant contact between the rotary wheel 106 and the underside 180 of the support flange 156. As the wear detection system 10 moves along the overhead conveyor system 134, the rotary wheel 106 rotates and the encoder 30 converts the angular position or motion of a shaft connected to the rotary wheel 106 to an analog or digital code. The encoder 30 may be absolute or incremental. The output of absolute encoders indicates the current position of the shaft, making them angle transducers. The output of incremental encoders provides information about the motion of the shaft, which can be processed by the integrated processing system 32 into position information.

The detecting sensor 28 is used to detect one or more yokes 148 and 150 of the overhead conveyor system 134. In particular, the detecting sensor 28 may be used by the integrated processing system 32 along with information from the encoder 30 to identify the presence of side-by-side yokes, which can be used to demarcate sections of the overhead conveyor system 134 and be used to provide accurate location information that is associated with the measurement information. For example, the detecting sensor 28 may detect presence of a yoke, which has a predetermined thickness (e.g., ¼ inch), which can be measured using the encoder 30 as the rotary wheel 106 travels along the underside 180 of the support flange 156 and the detecting sensor 28 detects yoke presence. If the integrated processing system 32 determines a yoke thickness of about the predetermined thickness or less, the integrated processing system 32 may determine a new section of the overhead conveyor system 134 is not present and essentially ignore the single yoke and continue collecting measurement and location information. On the other hand, if the integrated processing system 32 determines a yoke thickness of greater than the predetermined thickness, the integrated processing system 32 may determine that a new section of the overhead conveyor system 134 is present (e.g., a splice in the overhead conveyor system). In this instance, the integrated processing system 32 may reset or reinitialize the encoder 30 to begin anew (e.g., at zero distance) at the new section and/or change data storage locations for each section. While detection of yoke thickness may be used to detect sections of the overhead conveyor system 134, other section indicator markers may be used, such as indicator markers 188 that may be provided at an outer side 190 of the free rail member 144. In a fashion similar to the side-by-side yokes, the indicator markers 188 can have a thickness that is greater than a predetermined thickness to inhibit or prevent unintended section identifications. Indicators other than thickness may be used to identify sections of the overhead conveyor system 134, such as reflective tape, predetermined locations or distances along the overhead conveyor system 134 or any other suitable indicator, such as radio frequency identification (RFID) tags.

Figure 7:
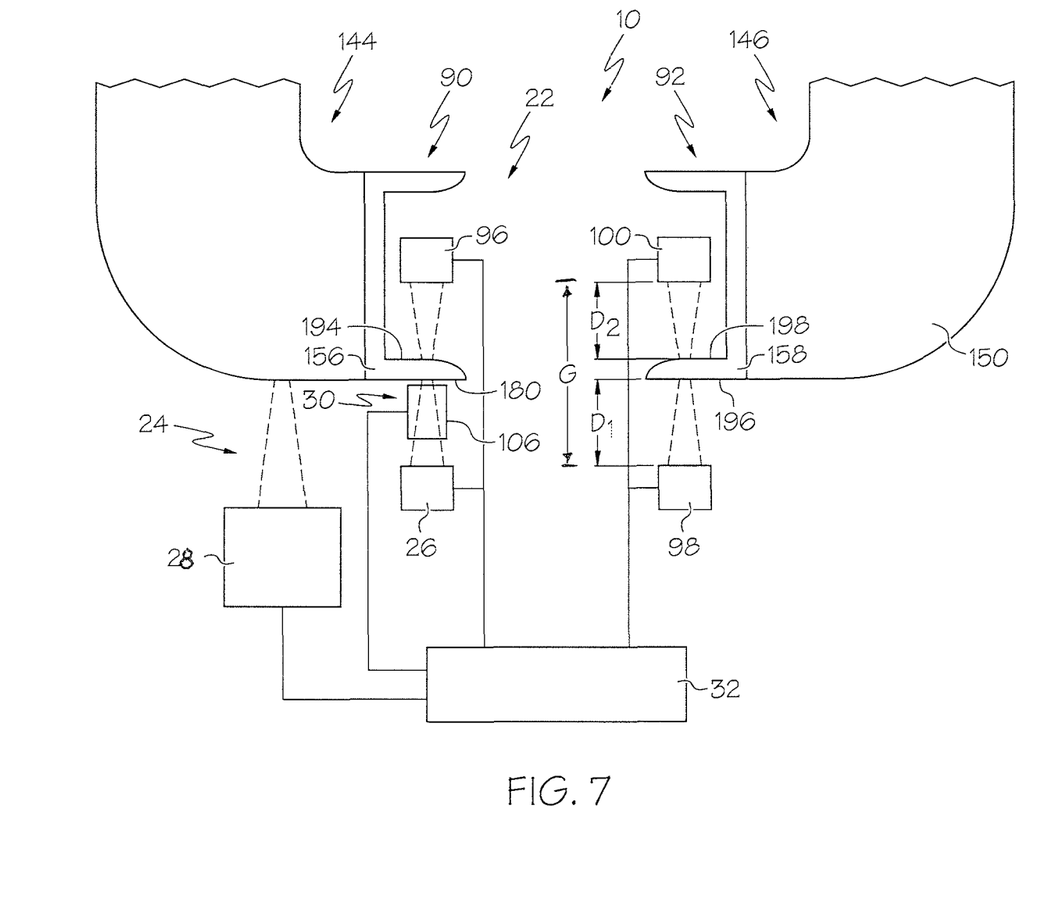
FIG. 7 illustrates operation of wear measurement and location detection systems of the wear detection system of FIG. 1 diagrammatically according to one or more embodiments described herein.

FIG. 7 illustrates operation of the wear measurement and location detection systems 22 and 24 diagrammatically with components of the wear detection system 10 shown in isolation for clarity. As the wear detection system 10 travels along the free rail members 144 and 146, the measuring sensor 26 of the laser displacement sensor pair 90 can be used to measure distance $D_1$ from the measuring sensor 26 to the underside 180 of the support flange 156 at a preselected location along the width of the support flange 156 and the measuring sensor 96 can be used to measure distance $D_2$ from the measuring sensor 96 to an upper side 194 of the support flange 156. Similarly, the measuring sensor 98 of the laser displacement sensor pair 92 can be used to measure distance $D_1$ from the measuring sensor 98 to an underside 196 of the support flange 158 at a preselected location along the width of the support flange 158 and the measuring sensor 100 can be used to measure distance $D_2$ from the measuring sensor 100 to an upper side 198 of the support flange 158. Knowing the size of gaps G, which may be the same (or different) and determined during calibration of the laser displacement sensor pairs 90 and 92, thicknesses $T_1$ and $T_2$ at the preselected locations can be determined by:

$$T=G-(D_1+D_2).$$

The measurement information determined using the wear measurement system 22 can be associated with location information determined using the location detection system 24. As the wear detection system 10 travels along the free rail members 144 and 146, the rotary wheel 106 of the encoder 30 rotates and the encoder 30 can report an incremental change in position to the integrated processing system 32 using a pulse. The pulses can be counted by the integrated processing system 32 to provide location (e.g., distance) information. For example, each pulse may indicate a predetermined distance travelled. As the pulses from the encoder 30 are counted by the integrated processing system 32, the detecting sensor 28 looks to detect presence of an indicator marker, such as the yoke 150. If the integrated processing system 32 detects a yoke thickness of greater than a predetermined thickness (e.g., thickness of a single yoke), the integrated processing system 32 may determine a new section is present and reset the encoder 30. In other words, the indicator marker or side-by-side yoke may provide a reference point to initialize a position measurement beginning at the new section of the overhead conveyor system 134.

Figure 8:
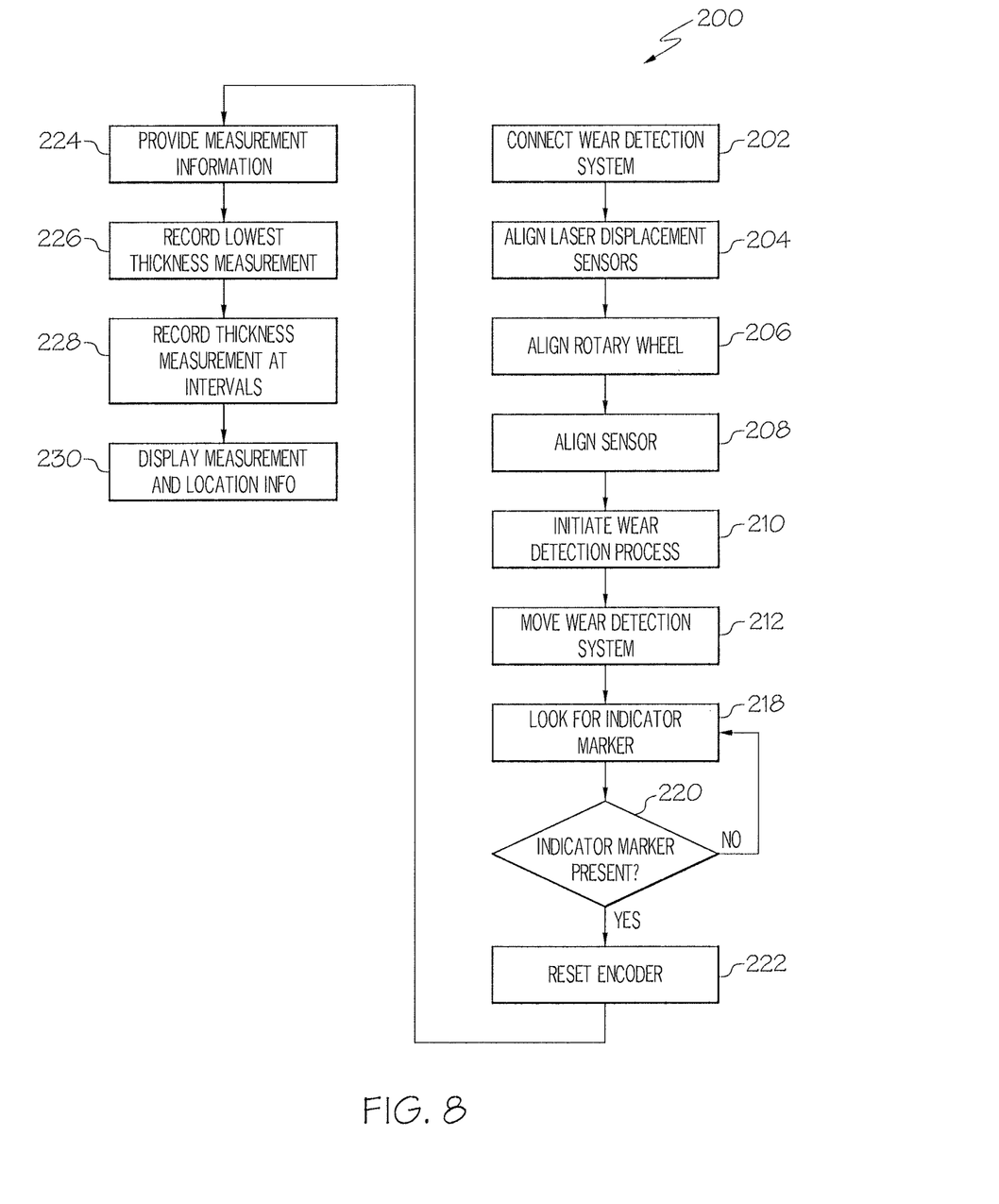
FIG. 8 illustrates a method of detecting wear along a support flange of a beam according to one or more embodiments described herein.

Referring to FIG. 8, a method 200 of detecting wear along a support flange of a beam is provided. As described above, the method 200 may be used to detect wear along support flanges of free rail members of overhead conveyor systems. At step 202, the rail riding portion 12 of the wear detection system 10 may be placed on the overhead conveyor system 134 with the wheels 18 supported on the support flanges 156 and 158. In some embodiments, turning or otherwise adjusting the axles 60 of the wheels 18 may facilitate insertion through the gap 160 (FIG. 5) between the support flanges 156 and 158 and placement of the wheels 18 on the support flanges 156 and 158. The positioning wheels 76 can be placed within the gap 160 and between the support flanges 156 and 158 thereby aiding in alignment of the laser displacement sensor pairs 90 and 92 and other components of the wear detection system 10, such as the encoder 30 and detecting sensor 28. In some embodiments, prior to connecting the wear detection system 10 to the overhead conveyor system 134, the laser displacement sensor pairs 90 and 92 may be calibrated.

Placing the rail riding portion 12 of the wear detection system 10 on the overhead conveyor system 134 may include aligning the laser displacement sensor pairs 90 and 92 above and below the support flanges 156 and 158 at step 204. At step 206, the rotary wheel 106 of the encoder 30 may be aligned with the underside 180 of the support flange 156 and biased thereagainst such that the rotary wheel 106 of the encoder rotates with movement of the wear detection system 10 of the overhead conveyor system 134. In some embodiments, the rotary wheel 106 may have a friction enhancing material applied thereon, such as a plastic or rubber tape that facilitates engagement between the rotary wheel 106 and the underside 180 of the support flange 156. At step 208, the detecting sensor 28 may be aligned somewhat outside the conveyor support volume 161 (FIG. 5) to detect the yokes, the side-by-side yokes being an indicator marker that a new section of overhead conveyor system is present.

A wear detection process is initiated at step 210. The wear detection process may be initiated using, for example, a personal computer or a hand-held device such as a tablet device, smart phone, etc. to communicate with the integrated processing system 32. In some embodiments, the wear detection process may be activated remotely, such as using an internet, cellular or intranet connection. In some embodiments, a particular wear detection process may be initiated automatically, such as at a certain time or upon occurrence of a particular event. At step 212, the wear detection system 10 moves along the overhead conveyor system 134. In some embodiments, the wear detection system 10 may utilize the power rail 152 (FIG. 4) of the overhead conveyor system 134. In these embodiments, the wear detection system 10 may be connected to the power line 155 of the power rail 152 using any suitable connection. In other embodiments, the wear detection system 10 may be provided with a motor that drives the wheels 18.

At step 218, the integrated processing system 32 looks for an indicator marker using detecting sensor 28, such as side-by-side yokes. If no indicator marker is detected at step 220, the integrated processor system 32 continues to look for an indicator marker using the detecting sensor 28. If an indicator marker is detected, the integrated processing system 32 resets or initiates the encoder 30 at a current section of the overhead conveyor system 134 at step 222. In some embodiments, a home position for the encoder 30, sensor and/or integrated processing system 32 may be provided. Such a home position can allow for initiation of the locating process, particularly where the encoder 30 is incremental. As one example, the home position of the wear detection system 10 may be at or near the beginning of a particular section, such as a first section of the overhead conveyor system 134. In some embodiments, the home position may be changed by identifying to the integrated processing system 32 at which section it will begin, for example, using a personal computer and/or handheld device.

At step 224, an output is provided by the laser displacement sensor pairs 90 and 92 to the integrated processing system 32. The integrated processing system 32 continuously monitors the output to detect and record in memory the lowest thickness measurement for each section and position of the lowest thickness reading within the particular section at step 226. At step 228, the integrated processing system 32 can also record thickness measurements at user specified intervals, such as at set distance intervals. A computer (FIG. 1) or other computing device in communication with the integrated processing system 32 may process the various sensor outputs and display the measurement and location information in a user-friendly format at step 230.

Figure 9:
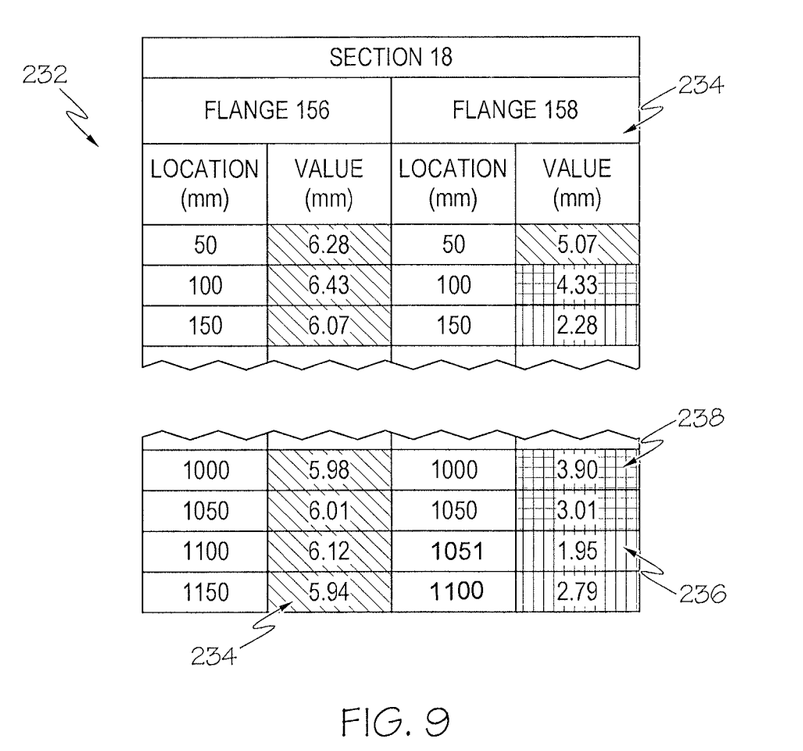
FIG. 9 illustrates an exemplary wear assessment table where thickness measurement and location information is displayed for a user according to one or more embodiments described herein.

For example, referring to FIG. 9, an exemplary wear assessment table 232 is illustrated where thickness measurement and location information 234 is saved in memory and displayed for a user. In this example, the thickness measurement and location information 234 are recorded for both support flanges 156 and 158 at 50 mm intervals. In addition to the 50 mm intervals, the lowest thickness measurement 236 is also recorded and displayed. In this example, the lowest thickness measurement occurs 1051 mm from the start or home position of Section 18 and is located outside the 50 mm intervals. While a 50 mm interval is illustrated, any desired interval may be used, such as between about 1 mm to about 1000 mm or any value less than 1 mm, between 1 mm and 1000 mm and greater than 1000 mm, depending on the desired output. In some embodiments, the wear assessment table 232 may include indicia 238, such as being color-coded, to highlight particular thickness values. As one example, an initial, unworn thickness of the support flanges 156 and 158 may be about 7.5 mm. Wear thickness values above a predetermined first wear thickness value (e.g., above about 4.5 mm) may be displayed green in color, wear thickness values between the first wear thickness value and a second wear thickness value (e.g., between about 4.5 mm and about 3 mm) may be displayed yellow in color, and wear thickness values below the second wear thickness value (e.g., below about 3 mm) may be displayed red in color. While color-coded indicia are illustrated, any suitable indicia may be used, such as flashing numerical values, font changes or other indicia.

Figure 10:
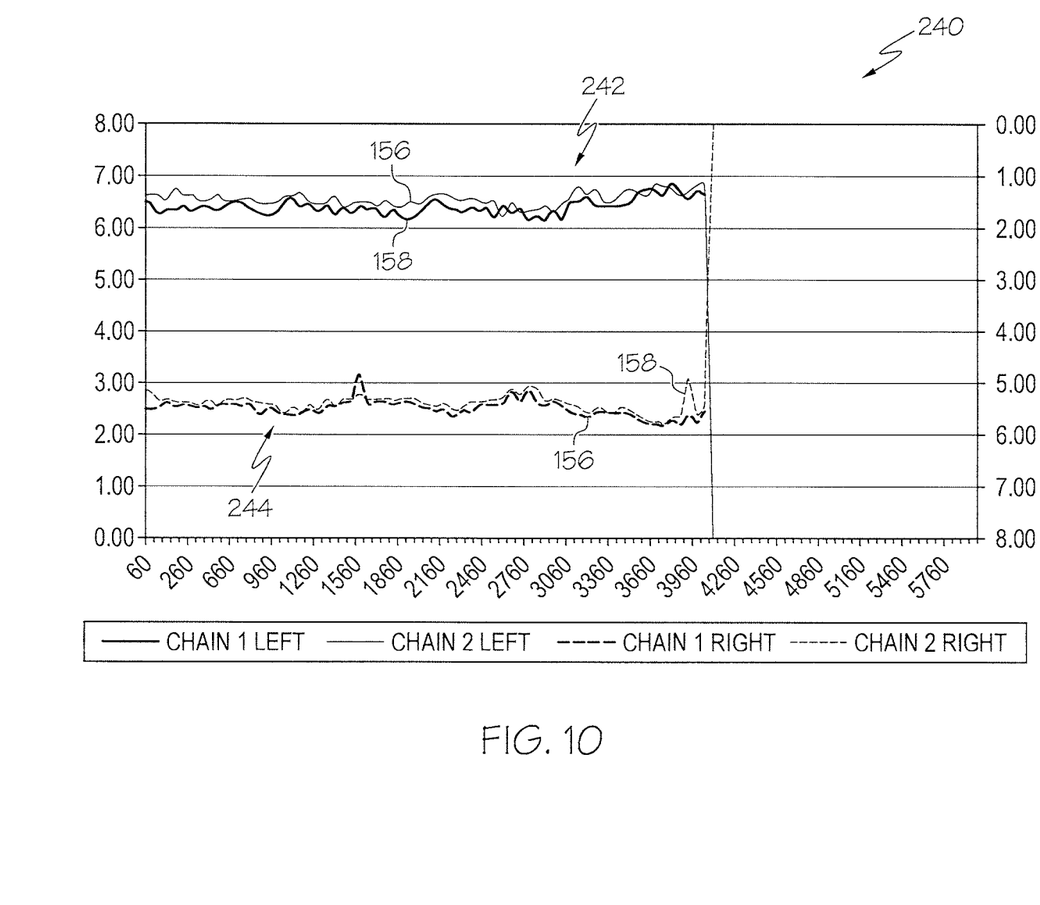
FIG. 10 illustrates an exemplary wear assessment chart where thickness measurement and location information is displayed for a user according to one or more embodiments described herein.

Referring to FIG. 10, thickness measurement information may be displayed in other useful formats. For example, a wear assessment chart 240 may be generated and displayed using any suitable computer or computing device in communication with the integrated processing system 32. In this example, two wear assessments 242 and 244 are displayed that occurred on different dates, with wear assessment 242 occurring first and wear assessment 244 occurring at a later date. As can be seen, wear assessment 244 illustrates wear occurring for the support flanges 156 and 158 over time compared to wear assessment 242.

The above-described wear assessment systems provide for automatically detecting wear along support flanges of overhead conveyor systems without any need to manually measure wear using a handheld device. The wear assessment systems not only provide measurement information, but also provide location information that pinpoint where particular thickness measurement values are taken. An integrated processing system is provided for processing the measurement and location information. The integrated processing system may travel with the wear assessment systems and be capable of communicating wirelessly with another computer or other computing device for further processing and/or saving of the location and measurement information. The location and measurement information may be displayed by the computer or other computing device in a user-friendly format such as in a table or chart.

While particular embodiments have been illustrated and described herein, it should be understood that various other changes and modifications may be made without departing from the spirit and scope of the claimed subject matter.

Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A wear detection system for detecting beam wear along a support flange of an overhead beam of an overhead conveyor system, the wear detection system comprising:
   a rail riding portion configured to hang within a channel of the overhead beam of the overhead conveyor system and travel along the support flange of the overhead beam with the rail riding portion at least partially within the channel; and
   a processor portion connected to the rail riding portion;
   the rail riding portion comprising a wear measurement system comprising one or more measuring sensor pairs configured to provide an output indicative of thickness of the support flange, wherein the one or more measuring sensor pairs comprise a first measuring sensor and a second measuring sensor in a face-to-face relationship above and below the support flange;
   the processor portion comprising an integrated processing system that receives the output of the one or more measuring sensor pairs and generates measurement information based on the output, the measurement information being indicative of wear on the support flange of the overhead beam.

2. The system of claim 1, wherein the rail riding portion comprises a frame and a sensor mount assembly that mounts the one or more measuring sensor pairs to the frame, the processor portion connected to the frame such that the processor portion hangs from the frame at a location below the overhead beam of the overhead conveyor system during a wear detection process.

3. The system of claim 1, wherein the rail riding portion includes one or more wheels arranged and configured to ride along the support flange of the overhead beam of the overhead conveyor system.

4. The system of claim 1, wherein the rail riding portion comprises an encoder having a rotary wheel that engages the support flange and is configured to provide an output indicative of location along the support flange of the overhead beam of the overhead conveyor system to the integrated processing system.

5. The system of claim 4, wherein the rail riding portion comprises a detecting sensor arranged and configured to detect an indicator marker and provide an output to the integrated processing system.

6. The system of claim 5, wherein the integrated processing system includes logic that resets the encoder based on output from the detecting sensor when the indicator marker is detected.

7. The system of claim 1, wherein the first measuring sensor is a first laser displacement sensor configured to be at least partially located within the channel of the overhead beam of the overhead conveyor system and the second measuring sensor is a second laser displacement sensor configured to be located underneath the support flange of the overhead beam of the overhead conveyor system.

8. A method for detecting beam wear along a support flange of an overhead beam of an overhead conveyor system using a wear detection system, the method comprising:
   moving a rail riding portion of the wear detection system hanging within a channel of the overhead beam of the overhead conveyor system along the support flange of the overhead beam with the rail riding portion at least partially within the channel, the wear detection system comprising a processor portion connected to the rail riding portion; generating an output indicative of thickness of the support flange using one or more measuring sensors of a wear measurement system carried by the rail riding portion; generating measurement information using an integrated processing system of the processor portion using the output of the one or more measuring sensors, the measurement information being indicative of wear on the support flange of the overhead beam; and providing an output to the integrated processing system indicative of location of the wear detection system along the support flange of the overhead beam of the overhead conveyor system using an encoder having a rotary wheel that engages an underside of the support flange; and wherein the encoder is biased into engagement with the underside of the support flange by the biasing arm, the integrated processing system generating location information based on the output of the encoder.

9. The method of claim 8 further comprising providing the location information to an external computer.

10. The method of claim 8 further comprising providing an output to the integrated processing system using a detecting sensor upon detecting an indicator marker.

11. The method of claim 10 further comprising the integrated processing system resetting the encoder based on the output from the detecting sensor when the indicator marker is detected.

12. The method of claim 8, wherein the one or more measuring sensors comprise a pair of laser displacement sensors.

13. The method of claim 8 further comprising providing the measurement information to an external computer.

14. The method of claim 13 further comprising reporting the measurement information to a user using the external computer.

15. The method of claim 14, wherein the measurement information is reported to a user using a mobile computing device.

16. A wear analysis system for detecting beam wear along a support flange of an overhead beam of an overhead conveyor system, the wear analysis system comprising:

a wear detection system comprising:
a rail riding portion configured to hang within a channel of the overhead beam of the overhead conveyor system and travel along the support flange of the overhead beam with the rail riding portion at least partially within the channel; and
a processor portion connected to the rail riding portion;
the rail riding portion comprising a wear measurement system comprising one or more measuring sensor pairs configured to provide an output indicative of thickness of the support flange, wherein the one or more measuring sensor pairs comprise a first measuring sensor and a second measuring sensor in a face-to-face relationship above and below the support flange;
the processor portion comprising an integrated processing system that receives the output of the one or more measuring sensor pairs and generates measurement information based on the output, the measurement information being indicative of wear on the support flange of the overhead beam; and
a computer external to the wear detection system that receives the measurement information and reports the measurement information to a user.

17. The wear analysis system of claim 16, wherein the computer is a mobile computing device.

18. The wear analysis system of claim 16, wherein the rail riding portion of the wear detection system comprises a frame and a sensor mount assembly that mounts the one or more measuring sensor pairs to the frame, the processor portion connected to the frame such that the processor portion hangs from the frame at a location below the overhead beam of the overhead conveyor system during a wear detection process.

19. The wear analysis system of claim 16, wherein the rail riding portion of the wear detection system comprises an encoder having a rotary wheel that engages the support flange and is configured to provide an output indicative of location along the support flange of the overhead beam of the overhead conveyor system to the integrated processing system.

* * * * *